US00PP14477P29

(12) United States Plant Patent
Head et al.

(10) Patent No.: US PP14,477 P2
(45) Date of Patent: Jan. 20, 2004

(54) ILEX PLANT NAMED 'HL10-90'

(50) Latin Name: *Ilex hybrid*
Varietal Denomination: HL10-90

(75) Inventors: Robert Harold Head, Seneca, SC (US); Lisa Jones Head, Seneca, SC (US); William Alan Head, Walhalla, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 10/313,124

(22) Filed: Dec. 6, 2002

(51) Int. Cl.[7] ..... A01H 5/00
(52) U.S. Cl. ..... Plt./247
(58) Field of Search ..... Plt./247

*Primary Examiner*—Kent Bell
(74) *Attorney, Agent, or Firm*—C. A. Whealy

(57) ABSTRACT

A distinct cultivar of Ilex plant named 'HL10-90', characterized by its columnar and compact growth habit; short internodes and very freely branching habit; dense and bushy plant habit; shiny dark green-colored leaves; large dark red-colored drupes; long-lasting red coloration; and hardy to USDA Hardiness Zone 6.

3 Drawing Sheets

Botanical classification/cultivar designation: Ilex hybrid cultivar HL10-90.

BACKGROUND OF THE INVENTION

The present Invention relates to a new and distinct cultivar of Ilex plant, botanically known as Ilex hybrid, and hereinafter referred to by the cultivar name 'HL10-90'.

The new Ilex originated from a cross-pollination of an unidentified selection of *Ilex pernyi*, not patented, as the female, or seed, parent with an unknown selection of Ilex hybrid, not patented, as the male, or pollen, parent. The new Ilex was discovered and selected as a single plant from the resulting progeny of the cross-pollination by the Inventors in a controlled environment in Seneca, S.C., in October, 1990.

Asexual reproduction of the new cultivar in a controlled environment by stem cuttings taken in Seneca, S.C., since January, 1996, has shown that the unique features of this new Ilex are stable and reproduced true to type in successive generations.

SUMMARY OF THE INVENTION

Plants of the cultivar HL10-90 have not been observed under all possible environmental conditions. The phenotype may vary somewhat with variations in environment such as temperature and light intensity without, however, any variance in genotype.

The following traits have been repeatedly observed and are determined to be the unique characteristics of 'HL10-90'. These characteristics in combination distinguish 'HL10-90' as a new and distinct cultivar:

1. Columnar and compact growth habit.
2. Short internodes and very freely branching habit; dense and bushy plant habit.
3. Shiny dark green-colored leaves.
4. Large dark red-colored drupes; long-lasting red coloration.
5. Hardy to USDA Hardiness Zone 6.

Plants of the new Ilex are most similar to the female parent, the unidentified selection of *Ilex pernyi*. However, in side-by-side comparisons conducted by the Inventors in Seneca, S.C., plants of the new Ilex differed from plants of the female parent selection in the following characteristics:

1. Plants of the new Ilex were more upright and not as spreading as plants of the female parent selection.
2. Plants of the new Ilex had shiny dark green-colored leaves whereas plants of the female parent selection had dull medium green-colored leaves.
3. Plants of the new Ilex had larger drupes than plants of the female parent selection.

Plants of the new Ilex can also be compared to plants of the Ilex hybrid cultivar China Girl, not patented. However, in side-by-side comparisons conducted by the Inventors in Seneca, S.C., plants of the new Ilex differed from plants of the cultivar China Girl in the following characteristics:

1. Plants of the new Ilex were more upright and not as outwardly spreading as plants of the cultivar China Girl.
2. Plants of the new Ilex had narrower and darker green-colored leaves than plants of the cultivar China Girl.
3. Plants of the new Ilex had larger and darker red-colored drupes than plants of the cultivar China Girl.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Ilex.

The photograph on the first sheet comprises a side perspective view of a typical 13-year old plant of 'HL10-90' grown in the ground in an outdoor nursery in Seneca, S.C.

The photograph on the second sheet comprises a close-up view of typical leaves and developing drupes of 'HLl0-90'.

The photograph on the third sheet comprises a close-up view of a typical stem with leaves, developing drupes and mature drupes of 'HL10-90'.

DETAILED BOTANICAL DESCRIPTION

In the following description, color references are made to The Royal Horticultural Society Colour Chart except where general terms of ordinary dictionary significance are used. Plants used for the description were about four years old and were grown in three-gallon containers in an unshaded outdoor nursery in Seneca, S.C. During the production of the plants day temperatures ranged from −5 to 40° C. and night temperatures ranged from −20 to 35° C.

Botanical classification: Ilex hybrid cultivar HL10-90.

Parentage:

*Female, or seed, parent.*—Unidentified selection of *Ilex pernyi*, not patented.

*Male, or pollen, parent.*—Unknown selection of Ilex hybrid, not patented.

Propagation:

*Type cutting.*—Stem cuttings.

*Time to initiate roots, summer.*—About 20 days at 27 to 30° C.

*Time to initiate roots, winter.*—About 40 days at 16 to 17° C.

*Time to produce a rooted cutting, summer.*—About 60 days at 27 to 30° C.

*Time to produce a rooted cutting, winter.*—About 90 days at 16 to 17° C.

*Root description.*—Thick, fibrous, white in color and freely branching.

Plant description:

*Form.*—Perennial evergreen broadleaf shrub; mostly upright, compact; columnar in overall shape.

*Plant height.*—Plants will be about 2 meters after 10 years.

*Plant diameter.*—Plants will be about 1.25 meters after 10 years.

*Branching habit.*—Very freely branching, lateral branches potentially developing at every node; short internodes; dense and bushy plant habit.

*Lateral branches.*—Length: Variable, about 2 to 18 cm. Diameter: About 1 to 3 mm. Internode length: About 3 to 13 mm. Shape: Cylindrical to oblong in cross-section. Strength: Strong; flexible. Angle: About 30 to 45° from vertical. Texture: Smooth, glabrous. Color: Young stems: 144A. Mature stems: 199B.

*Foliage description.*—Arrangement: Alternate. Length: Variable, about 2 to 5.5 cm. Width: Variable, about 7 to 20 mm. Shape: Narrow, oblong. Apex: Tricuspidate. Base: Cuneate to obtuse. Margin: Spinulose; undulate. Spines: About 7 to 14 per leaf; about 1 mm long; less than 1 mm wide; and 145B in color. Venation pattern: Pinnate. Texture, upper and lower surface: Smooth, glabrous; coriaceous, durable. Luster: Upper surface, glossy; lower surface, less glossy. Petiole length: About 4.5 mm. Petiole diameter: About 1.3 mm. Petiole texture, upper and lower surfaces: Smooth, glabrous. Color: Young leaves, upper surface: 139A. Young leaves, lower surface: 144A. Fully expanded leaves, upper surface: 136A. Fully expanded leaves, lower surface: 137B. Venation, upper surface: 141B. Venation, lower surface: 137B. Petiole: 141B.

Flower description:

*Flower type and habit.*—Single pistillate flowers arranged in axillary fasciculated cymes. Flowers persistent. Freely flowering with about three to six flowers per leaf node. Flowers face outward and upright. Fruit develop dark red coloration in December and maintain coloration until July in Seneca, S.C.

*Natural flowering season.*—Late spring; flowering continuous during this period.

*Flower longevity on the plant.*—About five to seven days.

*Fragrance.*—None detected.

*Flowers.*—Appearance: Small; rounded. Diameter: About 8 mm. Depth (length): About 4 mm.

*Flower buds.*—Length: About 3.5 mm. Diameter: About 2.8 mm. Shape: Spherical. Color: 145A.

*Petals.*—Quantity: Four per flower in a single whorl, not fused. Length: About 3.2 mm. Width: About 2.3 mm. Shape: Rotund. Apex: Rounded. Margin: Entire. Texture, upper and lower surfaces: Stiff; waxy; glabrous. Color: When opening, upper surface: 154C. When opening, lower surface: 154B. Fully opened, upper surface: 154D; color becoming closer to 150C with development. Fully opened, lower surface: 154C.

*Sepals.*—Arrangement/appearance: Four per flower in a single whorl; fused. Length: About 1 mm. Width: About 2 mm. Shape: Roughly triangular. Apex: Acute. Base: Fused. Margin: Entire. Texture, upper and lower surfaces: Smooth, glabrous. Color: Immature, upper surface: 144C. Immature, lower surface: 141C. Mature, upper and lower surfaces: 144B.

*Pedicels.*—Length: About 3.5 mm. Diameter: About 0.9 mm. Angle: About 45° from vertical. Strength: Strong. Color: 144B.

*Reproductive organs.*—Stamens: Quantity: Four per flower. Anther shape: Roughly cordate. Anther length: About 0.9 mm. Anther color: 155C. Pollen: None observed. Pistils: Quantity: One. Pistil length: About 0.1 mm. Stigma shape: Rounded, flat. Stigma color: 144C. Ovary color: 144B.

*Fruit.*—Type: Drupe. Length: About 8.8 mm. Diameter: About 9.5 mm. Shape: Spherical. Texture: Smooth, glabrous. Color: 46A.

*Seed.*—Quantity per fruit: About four. Length: About 5.3 mm. Diameter: About 3.8 mm. Color: 168C.

Disease/pest resistance: Plants of the new Ilex have not been noted to be resistant to specific pathogens and pests common to Ilex.

Weather tolerance: Plants of the new Ilex have been observed to be tolerant to rain, ice, snow and wind and tolerant to temperatures from −20 to higher than 40° C. Plants of the new Ilex are hardy to USDA Hardiness Zone 6.

It is claimed:

1. A new and distinct cultivar of Ilex plant named 'HL10-90', as illustrated and described.

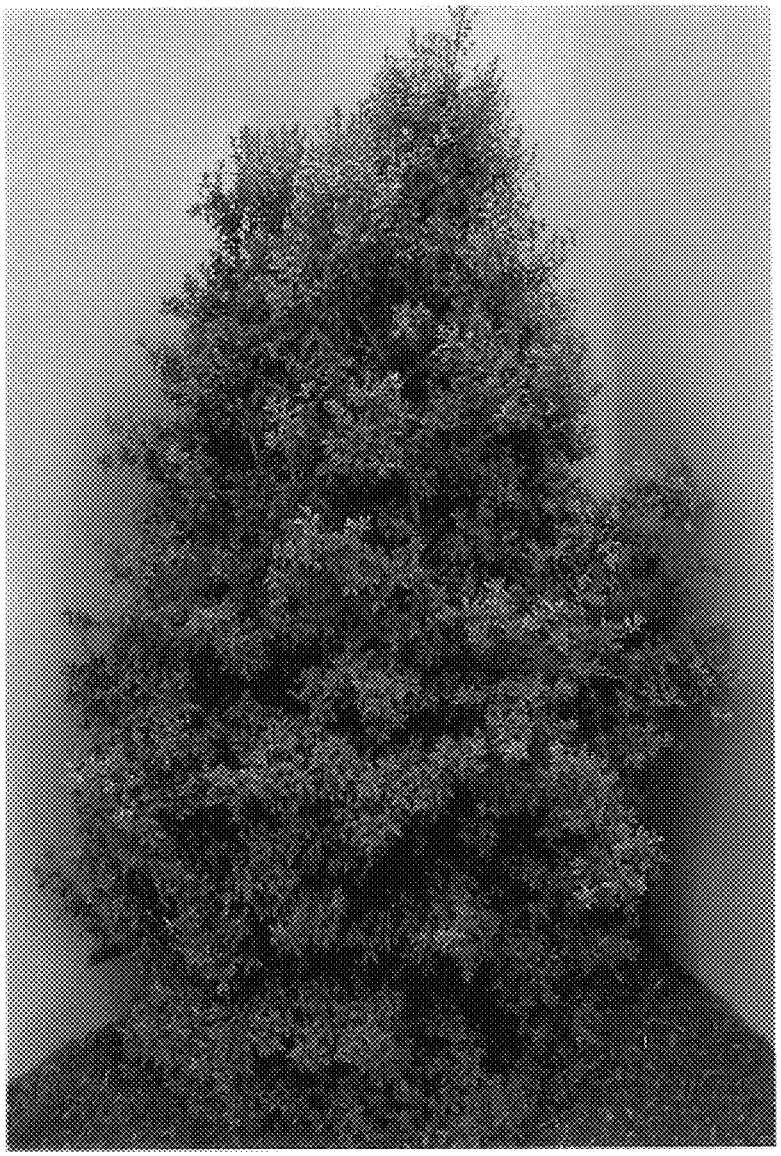

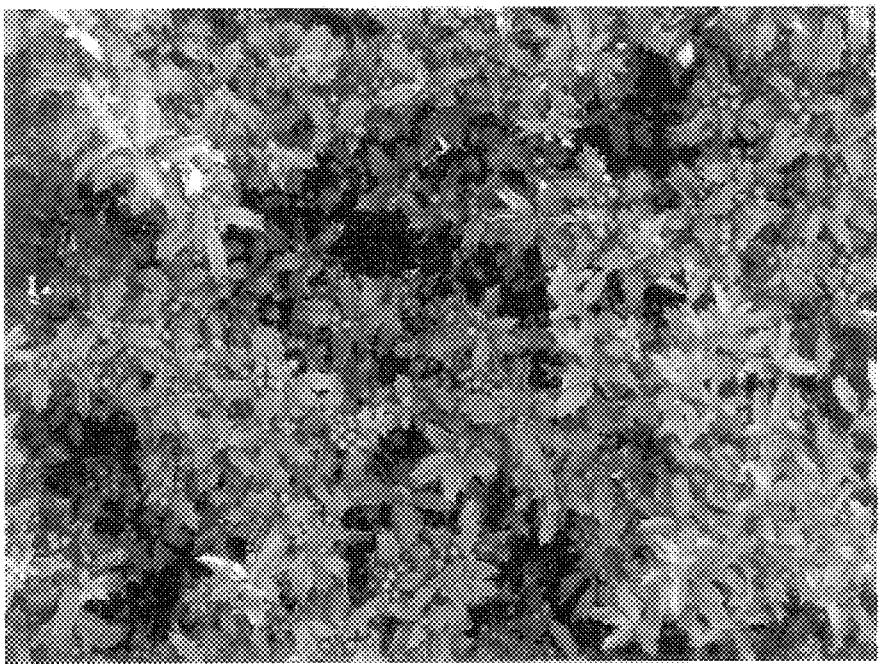

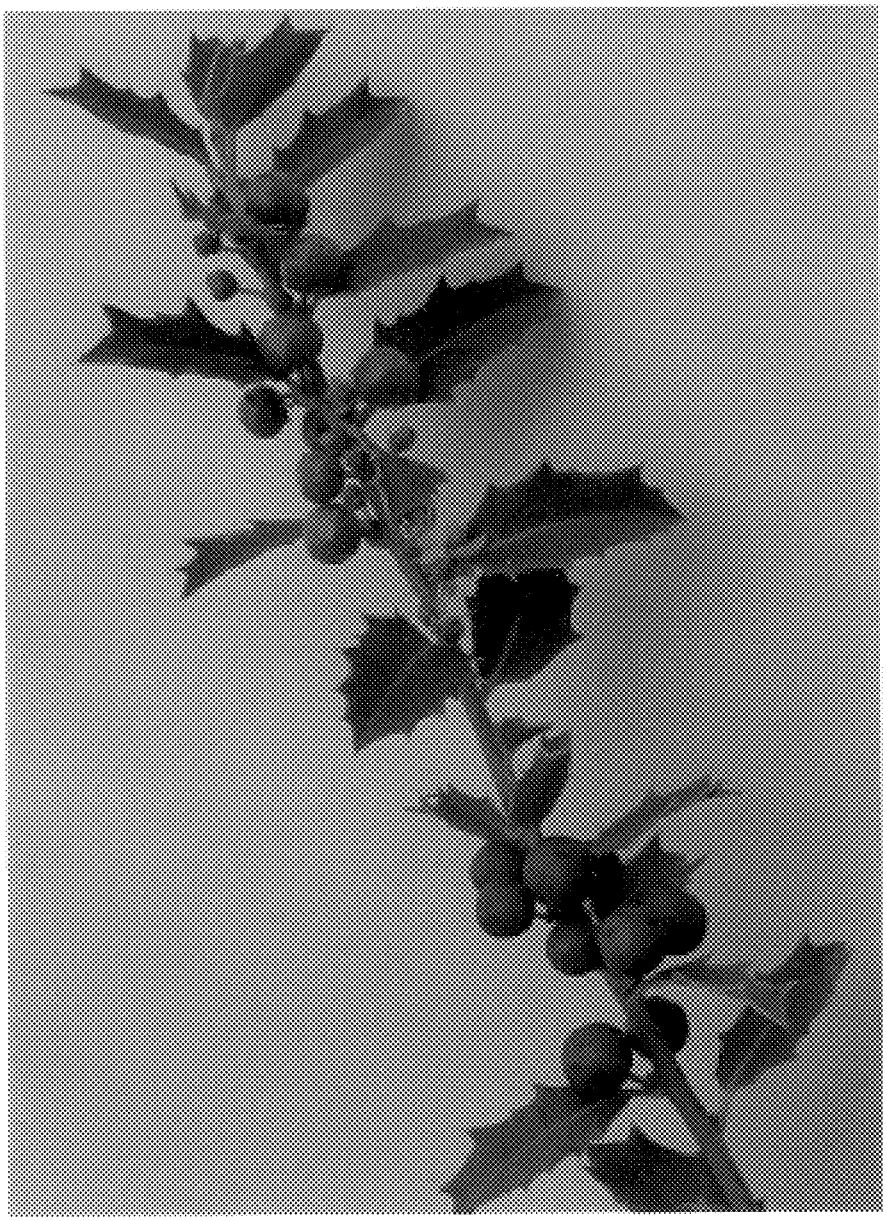

* * * * *